(12) United States Patent
Tairaku

(10) Patent No.: US 10,028,805 B2
(45) Date of Patent: Jul. 24, 2018

(54) ORTHODONTIC RETAINER

(71) Applicant: Tadateru Tairaku, Yokohama (JP)

(72) Inventor: Tadateru Tairaku, Yokohama (JP)

( * ) Notice: Subject to any disclaimer, the term of this patent is extended or adjusted under 35 U.S.C. 154(b) by 0 days.

(21) Appl. No.: 14/781,203

(22) PCT Filed: Jan. 21, 2014

(86) PCT No.: PCT/JP2014/051033
§ 371 (c)(1),
(2) Date: Jan. 13, 2016

(87) PCT Pub. No.: WO2014/156238
PCT Pub. Date: Oct. 2, 2014

(65) Prior Publication Data
US 2016/0120620 A1 May 5, 2016

(30) Foreign Application Priority Data

Mar. 29, 2013 (JP) ................. 2013-072247

(51) Int. Cl.
*A61C 11/00* (2006.01)
*A61C 7/08* (2006.01)

(52) U.S. Cl.
CPC ..................... *A61C 7/08* (2013.01)

(58) Field of Classification Search
CPC ...................................... A61C 7/08
USPC .................................. 433/60, 6, 7
See application file for complete search history.

(56) References Cited

U.S. PATENT DOCUMENTS

| 4,253,828 | A | * | 3/1981 | Coles | A61C 7/00 |
| | | | | | 433/6 |
| 4,413,978 | A | | 11/1983 | Kurz | |
| 5,536,169 | A | | 7/1996 | Yousefian | |
| 2005/0100853 | A1 | * | 5/2005 | Tadros | A61C 19/063 |
| | | | | | 433/6 |
| 2006/0078840 | A1 | * | 4/2006 | Robson | A61C 7/08 |
| | | | | | 433/6 |

(Continued)

FOREIGN PATENT DOCUMENTS

| JP | 2003-038520 | 2/2003 |
| JP | 3470800 | 11/2003 |

(Continued)

OTHER PUBLICATIONS

International Search Report for PCT/JP2014/051033, dated Feb. 10, 2014, and English translation, 4 pages total.

*Primary Examiner* — Cris L Rodriguez
*Assistant Examiner* — Mirayda A Aponte
(74) *Attorney, Agent, or Firm* — Hamre, Schumann, Mueller & Larson, P.C.

(57) ABSTRACT

The present invention addresses the problem of providing an orthodontic retainer with which there are no aesthetic concerns and smooth pronunciation during conversation is possible, and which is able to secure favorable fitting and can be worn for long periods. The retainer is configured so that, by being fitted so as to surround the entire dental arch (T) of the maxilla (A) or the mandible and by the inner surface being fitted, on the front and back surfaces of the entire dental arch (T), with a specified vertical width (H) that encompasses the cervical sections (T1, T2) of said teeth, a retaining force is applied on a portion of the crown (T3) of each tooth from the front and back surfaces.

3 Claims, 6 Drawing Sheets

(56) References Cited

U.S. PATENT DOCUMENTS

2008/0268400 A1* 10/2008 Moss .................. A61C 7/00
433/24
2011/0129786 A1* 6/2011 Chun .................. A61C 7/08
433/19
2013/0298916 A1* 11/2013 Alvarez ................ A61O 5/14
128/861

FOREIGN PATENT DOCUMENTS

JP          3637380      4/2005
JP          5006890      8/2012

* cited by examiner

ORTHODONTIC RETAINER

TECHNICAL FIELD

The present invention relates to an orthodontic retainer attached to the dental arch after orthodontic treatment for use in maintaining the dental arch and the width diameter, retaining occlusal stability, and preventing reversion.

BACKGROUND ART

Conventionally, in orthodontic treatment, an irregular dental arch is corrected by an orthodontic device moving teeth to appropriate positions, and the orthodontic device has to be removed after treatment. With removal of the device, the dental arch, the width diameter, and occlusion that has been fixed by the device become unstable because they are approaching positions before treatment (the corrected teeth tend to return to an original position).

For this reason, an orthodontic retainer is attached to the dental arch after treatment and, with this orthodontic retainer, in place of the orthodontic device, the teeth subjected to orthodontics are retained at positions after orthodontic treatment (refer to Patent Literature 1).

And, the above-described orthodontic retainer has to be continuously attached for a period until the positions of the teeth subjected to orthodontics become stable.

CITATION LIST

Patent Literature

PTL 1: Japanese Unexamined Patent Application Publication No. 2003-38520

SUMMARY OF INVENTION

Technical Problem

The above-described conventional orthodontic retainer is configured to hold the front side of the dental arch with wires and hold the inside of the dental arch with a plate formed of resin.

Meanwhile, an object of the orthodontic retainer is to stabilize the dental arch and prevent reversion after orthodontic treatment and, for this purpose, the orthodontic retainer is required to be always attached. However, the attachment ratio of the orthodontic retainer with the above-described conventional structure tends to be low.

One reason for this is that since the wires are positioned on the front surface of the dental arch and these wires are positioned approximately at the center of the tooth crown of the dental arch, for example, the wires are exposed in conversation, which does not provide an aesthetically favorable impression.

Moreover, it has been suggested that since the wires are intervened between the dental arch and the lips, it is difficult to pronounce and attachment feeling is unfavorable. Furthermore, the resin on a palate side touches the tongue to not only make it difficult to pronounce but also cause a vomiting reflex.

In view of these problems unsolved in the conventional technology, the present invention is to provide an orthodontic retainer which allows smooth pronunciation in conversation and long-time attachment by ensuring favorable attachment feeling without concerns regarding an aesthetic aspect.

Solution to Problem

To solve the above-described problems, an orthodontic retainer according to claim 1 of the present invention is an orthodontic retainer to be attached to a dental arch after orthodontic treatment to retain positions of the teeth after orthodontic treatment, wherein the orthodontic retainer is attached to surround entirety of the dental arch of an upper jaw or a lower jaw and has an inner surface intimately contacted with upper and lower portions on front and back surfaces of the entirety of the dental arch with a predetermined width across tooth cervix parts of these surfaces, thereby applying a constraint force to a part of a tooth crown of each of the teeth from the front and back surfaces.

According to the orthodontic retainer according to claim 1 of the present invention, by positioning this orthodontic retainer near the tooth cervix parts of each tooth of the dental arch, the attachment position can be made closer to the gums to minimize exposure in pronunciation and the like, and an impairment of an aesthetic aspect can be inhibited.

Also, since portions near the tooth cervix parts are constrained and these portions near the tooth cervix parts are positions near the root on a lip's inner side, movements of the lips are less inhibited, thereby allowing smooth pronunciation.

At the same time, a sense of togetherness with the gums can be obtained, thereby allowing long-time attachment together with mitigation of an uncomfortable feeling at the time of attachment.

In the orthodontic retainer according to claim 2 of the present invention, a width of an intimate contact with the tooth crown according to claim 1 is set to be equal to or smaller than half of a height from the tooth cervix to the tooth crown.

With this structure, exposure in pronunciation and the like can be effectively inhibited, and an effect of inhibiting an uncomfortable feeling at the time of attachment can be more enhanced.

In the orthodontic retainer according to claim 3 of the present invention, the orthodontic retainer according to claim 1 or claim 2 is a resin-molded product.

With this structure, appropriate elasticity can be provided to the orthodontic retainer, thereby allowing detachment and attachment to be facilitated and deformation with the detachment and attachment, for example, occurrence of looseness or the like, to be inhibited.

Also, with the resin being, for example, transparent, colored-transparent, or colored similarly to the gums, the orthodontic retainer can be made more inconspicuous to enhance aesthetic.

Advantageous Effects of Invention

According to the present invention, an orthodontic retainer can be provided which does not give concerns regarding an aesthetic aspect, allows smooth pronunciation in conversation, and allows favorable attachment feeling to be ensured.

DESCRIPTION OF EMBODIMENTS

An embodiment of the present invention is described below with reference to the drawings.

Figure 2:
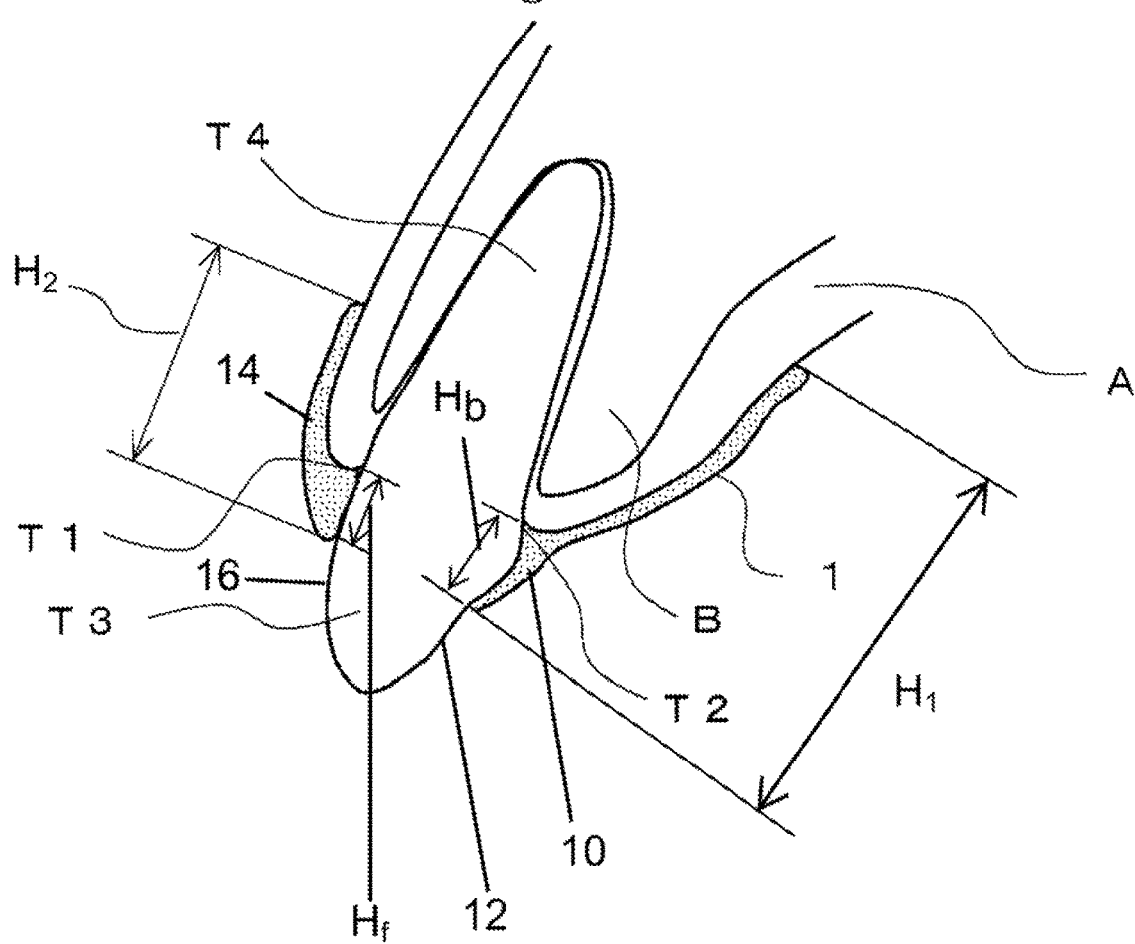
FIG. 2 depicts one embodiment of the present invention, and is a longitudinal cross-sectional view of main parts when attached to the dental arch of the upper jaw.
Figure 3:
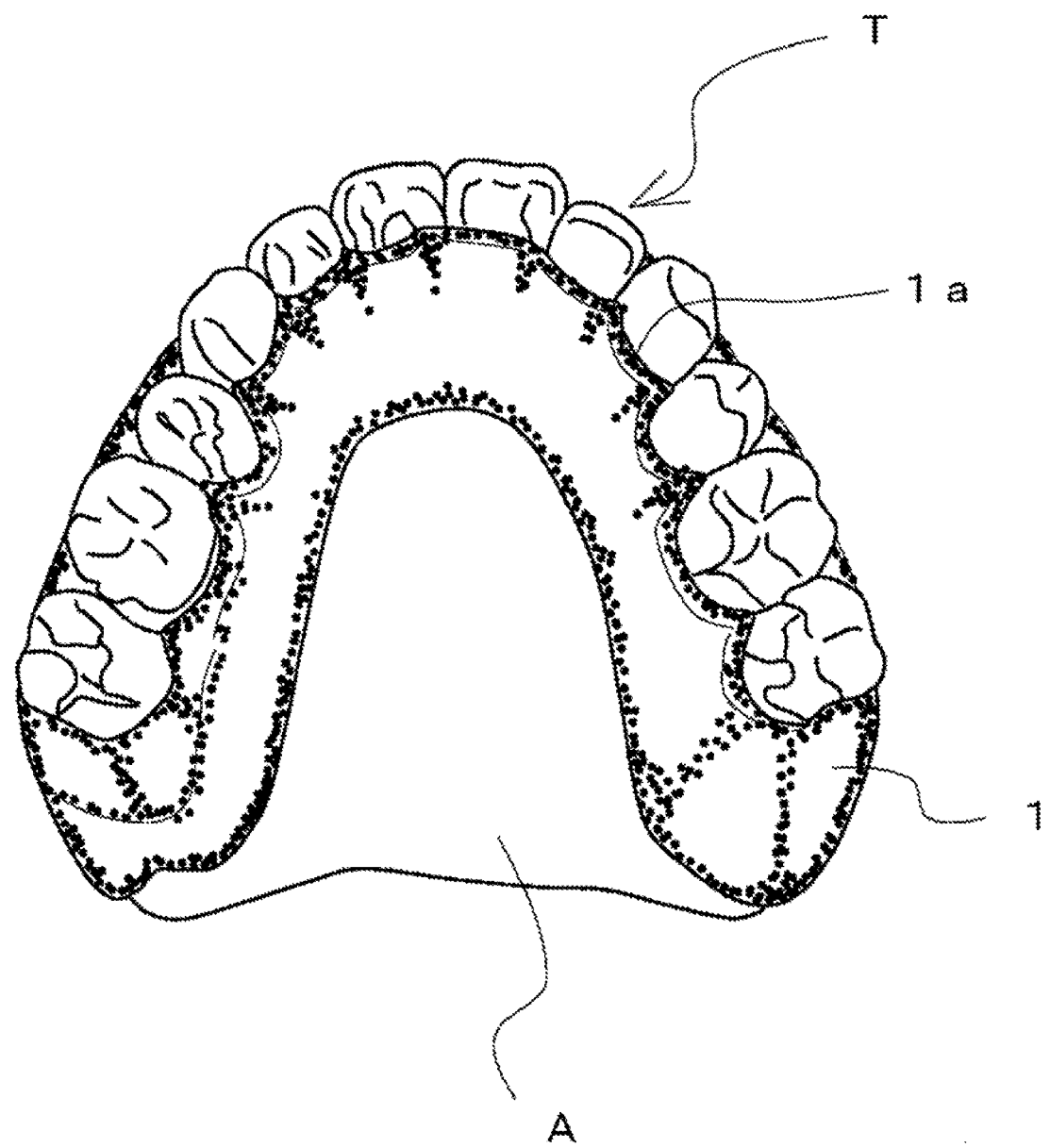
FIG. 3 depicts one embodiment of the present invention, and is a diagram when the state of being attached to the dental arch of the upper jaw is viewed from below.
Figure 4:
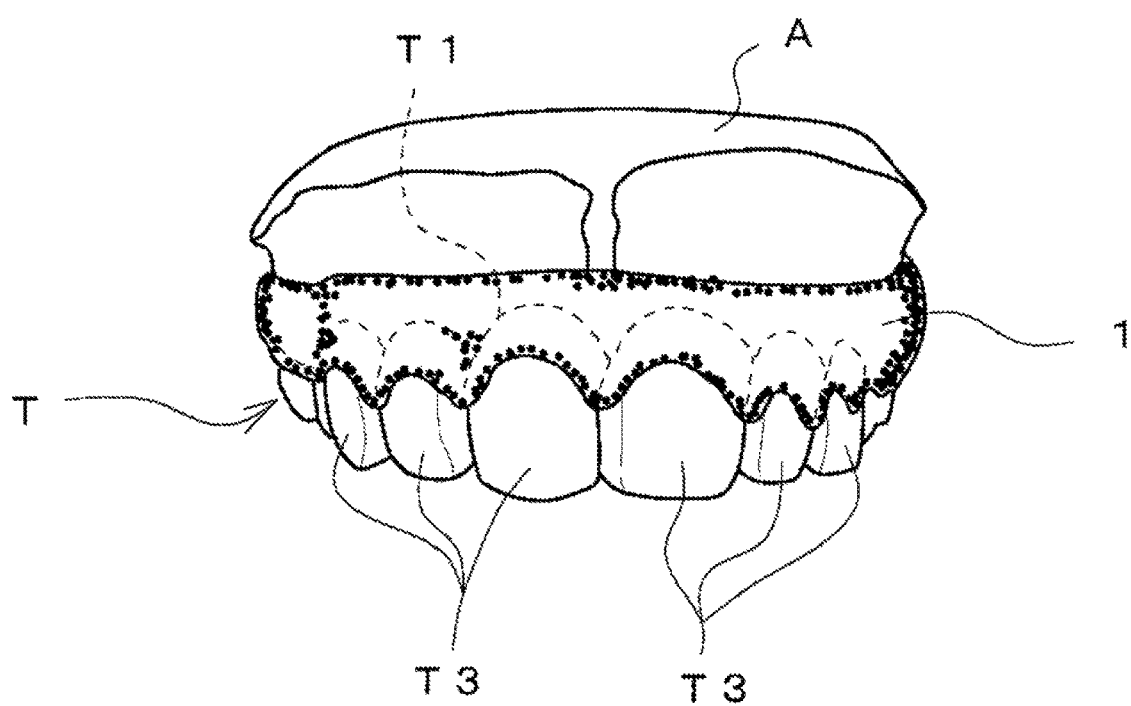
FIG. 4 depicts one embodiment of the present invention, and is a diagram when the state of being attached to the dental arch of the upper jaw is viewed from front.
Figure 5:
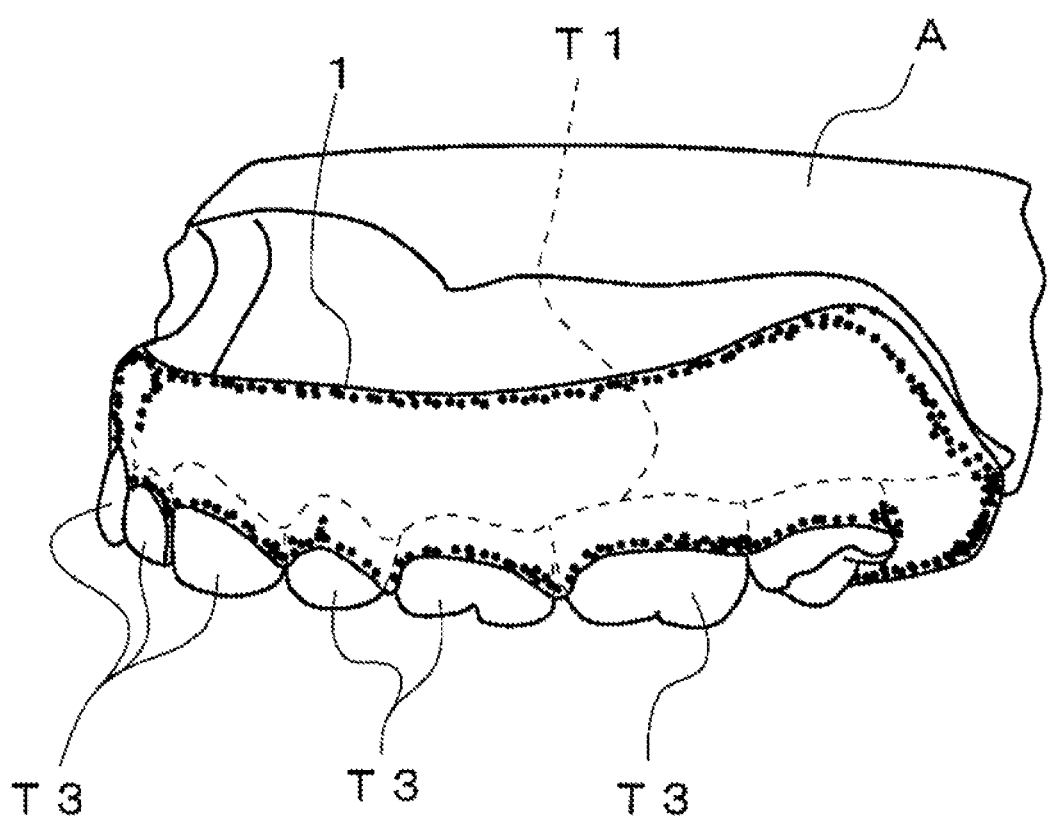
FIG. 5 depicts one embodiment of the present invention, and is a diagram when the state of being attached to the dental arch of the upper jaw is viewed from a side.

In these drawings, an orthodontic retainer denoted by a reference number 1 according to the present embodiment (hereinafter abbreviated as a retainer) is applied to an upper jaw A (refer to FIG. 3 to FIG. 5). This retainer 1 is attached to surround an entire dental arch T of the upper jaw A, and has an inner surface 1a intimately contacted with upper and lower portions on front and back surfaces of the entire dental arch T with a predetermined vertical width H across tooth cervix parts T1 and T2 of these surfaces, thereby, as depicted in FIG. 2, applying a constraint force to a part of a tooth crown T3 of each of the teeth from the front and back surfaces.

In the present embodiment, a width of an intimate contact between the retainer 1 and each tooth crown T3 is set at approximately one thirds of a height from the tooth cervix part T1 to the tooth crown T3.

This width of the intimate contact between the retainer 1 and each tooth crown T3 can be in a range of one tenth to half of the height of the tooth crown T3, preferably from one fifth to half thereof, and more preferably from one fourth to one thirds thereof.

Also, to provide aesthetic consideration, this width of the intimate contact between the retainer 1 and each tooth crown T3 is preferably set to be equal to or smaller than half of the height of the tooth crown T3. Furthermore, to provide consideration regarding the constraint force for the tooth crown T3, this width of the intimate contact is preferably set to be equal to or larger than one tenth of the height of the tooth crown T3.

Figure 1:
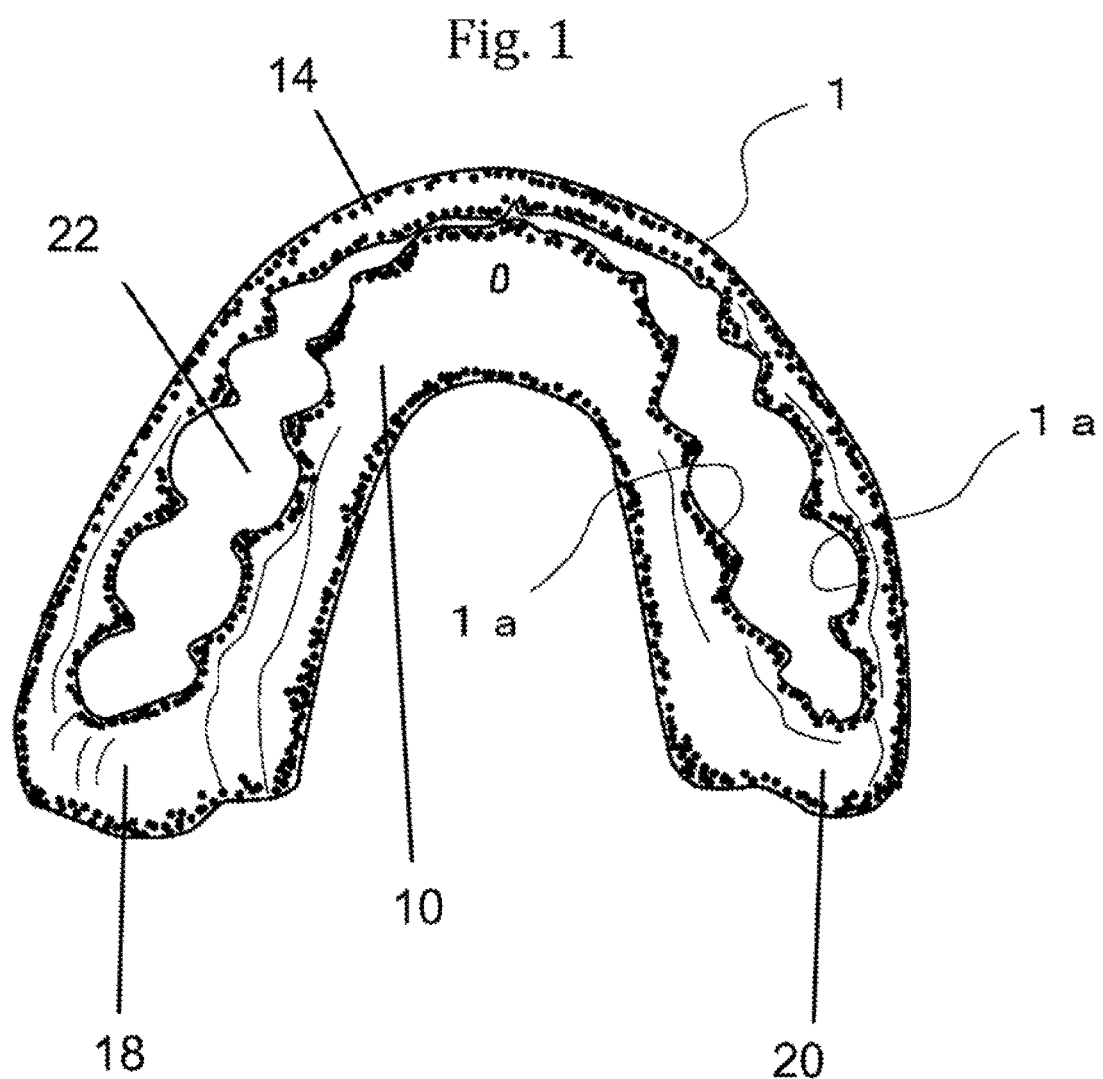
FIG. 1 is a plan view of one embodiment of the present invention.

Referring to FIGS. 1 and 2, the retainer 1 includes a back retainer portion 10 with the inner surface 1a thereof being configured to contact back surfaces 12 of the teeth over the entire dental arch T over a back vertical width $H_b$ of the teeth. The retainer 1 further includes a front retainer portion 14 with the inner surface 1a thereof being configured to contact front surfaces 16 of the teeth over the entire dental arch T over a front vertical width $H_f$ of the teeth. The inner surface 1a of the back retainer portion 10 has a first vertical width $H_1$, the inner surface 1a of the front retainer portion 14 has a second vertical width $H_2$, and the first vertical width $H_1$ is greater than the second vertical width $H_2$. Retainer connecting portions 18, 20 connect the back retainer portion 10 to the front retainer portion 14. A single, continuous opening 22 is thereby formed through the retainer 1 between the inner surface 1a of the back retainer portion 10, the inner surface 1a of the front retainer portion 14, and the retainer connecting portions 18, 20. The opening 22 extends over the entire dental arch T allowing the portions T3 of the teeth of the dental arch T to extend through the retainer 1 without the portions T3 being covered by the inner surface 1a of the back retainer portion 10 or the inner surface 1a of the front retainer portion 14. Moreover, the retainer 1 is made only of resin.

Furthermore, in the present embodiment, the retainer 1 is formed by molding polyester resin. In the present embodiment, as polyester resin, one being used as an aesthetic dental plate material is used. This is because this polyester resin has appropriate elasticity in a state of being molded as the retainer 1.

Note that, as the resin, other than polyester-based resin, those being used as a material for dental plates can be appropriately selected for use, such as polyamide-based, polycarbonate-based, acrylic-based, and polyalkylene-based resins.

The retainer 1 according to the present embodiment is formed by taking a mold of the dental arch T after orthodontic treatment to create a work model and, with this work model taken as an inner mold, covering an outer mold around the inner mold, and injecting polyester resin into a space between these inner mold and outer mold.

Alternatively, the retainer is formed by injection by pressing polyester resin before curing around the denture to straighten up the outer appearance and then curing the resin.

The inner surface 1a of the retainer 1 formed in this manner has a shape identical to the shape of the dental arch T on the front and back surfaces in the range of the predetermined width across the tooth cervix parts T1 and T2 on the front and back surfaces of the dental arch T.

And, by using its appropriate elasticity, the molded retainer 1 is attached to the dental arch after treatment so as to surround the dental arch T and the side surface of the gingiva. After attachment, its inner surface is intimately contacted with the tooth crown T3 and the gingiva in the range of the predetermined with H across the tooth cervix parts T1 and T2 on the front and back of the entire teeth of the dental arch T.

In this state, a maintaining force of the retainer acts on the dental arch T to retain this dental arch T at a position after orthodontic treatment.

Also, with the retainer 1 and the dental arch T in intimate contact with each other on its inner and outer surfaces, a state of engagement with an undercut portion of the dental arch T is generated. Furthermore, with the occurrence of viscosity with oral mucosa, the retainer 1 is fixed to its attachment position.

Figure 6:
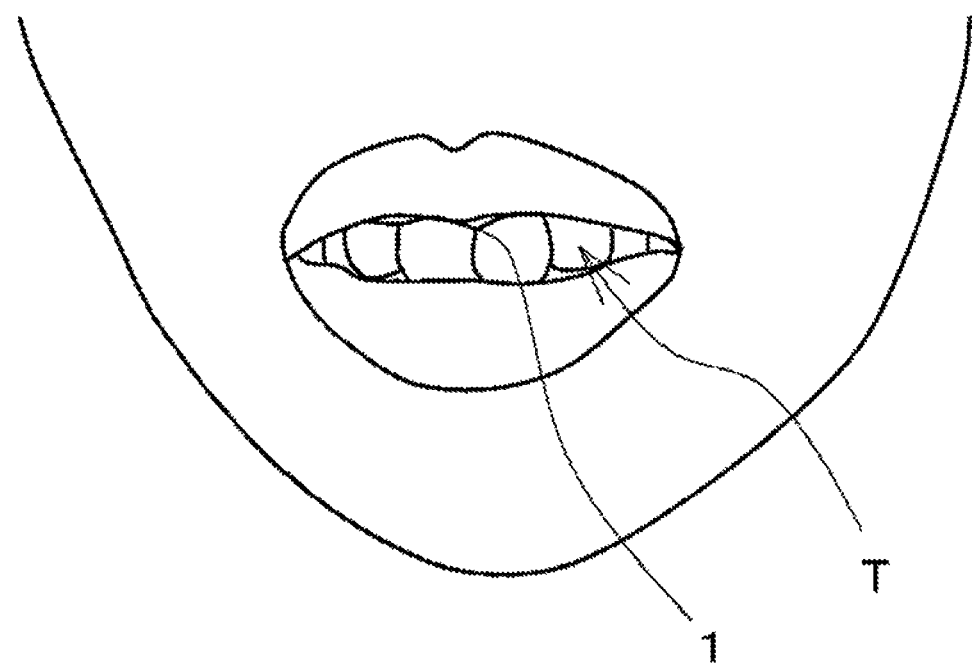
FIG. 6 depicts one embodiment of the present invention, and is a diagram when the state around the mouth with the embodiment attached to the dental arch of the upper jaw is viewed from front.

And, after attachment, since the attachment position is near the gums, exposure in pronunciation and the like can be minimized as depicted in FIG. 6, and an impairment of an aesthetic aspect can be inhibited.

Also, since portions near the tooth cervix parts T1 and T2 are constrained and these portions near the tooth cervix parts T1 and T2 are positions near the root on a lips inner side, movements of the lips and the tongue are less inhibited, thereby allowing smooth pronunciation.

At the same time, a sense of togetherness with the gums can be obtained, thereby allowing long-time attachment together with mitigation of an uncomfortable feeling at the time of attachment.

And, with the resin as a material for forming the retainer 1 being transparent, colored-transparent, or colored similarly to the gums, the retainer can be made more inconspicuous.

REFERENCE SIGNS LIST 1 (orthodontic) retainer
1a inner surface

A upper jaw
B alveolar bone
H width (of an intimate contact)
T dental arch
T1 tooth cervix part
T2 tooth cervix part
T3 tooth crown
T4 tooth root

The invention claimed is:

1. An orthodontic retainer configured for attachment to a dental arch of an upper jaw or a lower jaw after orthodontic treatment to retain a corrected position of teeth of the dental arch, comprising:
- a back retainer portion with an inner surface that is configured to contact back surfaces of the teeth and an inner gum of the dental arch over the entire dental arch over a back vertical width of the teeth;
- a front retainer portion with an inner surface that is configured to overlap and extend over front surfaces of the teeth in intimate contact therewith and overlap and extend over an edge and a front facing surface of an outer gum of the dental arch over the entire dental arch;
- a width of the intimate contact between the front retainer portion and the front surfaces of the teeth is set in a range of one fifth to half of a height from a tooth cervix part to a tip of a tooth crown, where the intimate contact starts from the tooth cervix part in a direction toward the tip of the tooth crown;
- an edge of the front retainer portion that faces in a direction toward the tip of the tooth crown is non-linear with a plurality of peaks and valleys;
- retainer connecting portions that connect the back retainer portion to the front retainer portion; and
- a single, continuous opening formed through the orthodontic retainer between the inner surface of the back retainer portion, the inner surface of the front retainer portion, and the retainer connecting portions; the opening extending over the entire dental arch allowing portions of the teeth of the dental arch to extend through the orthodontic retainer without being covered by the inner surface of the front retainer portion,
- wherein the orthodontic retainer is made only of resin.

2. The orthodontic retainer according to claim 1, wherein the resin is a polyester resin.

3. The orthodontic retainer according to claim 1, wherein the inner surface of the back retainer portion has a first vertical width, the inner surface of the front retainer portion has a second vertical width, and the first vertical width is greater than the second vertical width.

* * * * *